United States Patent [19]
Chang et al.

[11] Patent Number: 5,531,116
[45] Date of Patent: Jul. 2, 1996

[54] APPARATUS AND METHOD FOR PHASE TOMOGRAPHIC DETERMINATION OF FLUID CURRENTS

[75] Inventors: David B. Chang, Tustin; Victor Vali, Laguna Hills; Donald H. Webb, Torrance, all of Calif.

[73] Assignee: Hughes Aircraft Company, Los Angeles, Calif.

[21] Appl. No.: 180,266

[22] Filed: Jan. 12, 1994

[51] Int. Cl.⁶ .................................................. G01F 1/66
[52] U.S. Cl. ................................. 73/597; 73/861.27
[58] Field of Search ........................... 73/596, 597, 625, 73/628, 861.27, 861.18, 861.28; 340/606

[56] References Cited

U.S. PATENT DOCUMENTS

| | | | |
|---|---|---|---|
| 2,949,772 | 8/1960 | Kritz | 73/861.27 |
| 2,949,773 | 8/1960 | Batchelder | 73/861.27 |
| 4,262,545 | 4/1981 | Lamarche | 73/861.27 |
| 4,663,977 | 5/1987 | Vander Heyden | 73/861.27 |

FOREIGN PATENT DOCUMENTS 2235294  2/1991  United Kingdom ..................... 73/592

OTHER PUBLICATIONS

Somerstein et al., "Radio–frequency geotomography for remotely probing the interiors of operating mini— and commercial–sized oil–shale retorts."; Geophysics, vol. 49, No. 8 (Aug. (1984); pp. 1288–1300, 13 Figs.

*Primary Examiner*—Hezron E. Williams
*Assistant Examiner*—Christine K. Oda
*Attorney, Agent, or Firm*—Georgann S. Gruneback; Wanda K. Denson

[57] ABSTRACT

An array of acoustic signal sources and sensors are positioned in a fluid. Acoustic signals propagated through the medium are subjected to phase differences as they pass through fluid currents. An eikonal description of the acoustic waves propagating through the fluid medium is used to derive the fluid currents. Fluid currents are measured in a multiplicity of acoustic paths extending from the acoustic sources to the sensors, using acoustic phase tomography.

14 Claims, 2 Drawing Sheets

APPARATUS AND METHOD FOR PHASE TOMOGRAPHIC DETERMINATION OF FLUID CURRENTS

BACKGROUND OF THE INVENTION

1. Field of the Invention

This invention relates to a method and apparatus for measuring fluid currents, particularly water currents, in order to obtain surface or bulk current distributions. More particularly, this invention relates to the use of accoustic transmissions in fluids, with eikonal approximations and tomographic techniques used to derive current measurement from the phase information of acoustic signals.

2. Description of the Related Art

There exists a need for on-site determination of water currents. Knowledge of water currents is important in monitoring and predicting conditions in various marine ecosystems, including fisheries. Such knowledge can also be beneficial in determining the transport of sediment and pollutants. Knowledge of pollutant transport can help to mitigate damage to fisheries and other wildlife habitats.

Previous methods for determining currents have included flow meters and high-frequency radar. Flow meters can provide on-site measurements, but not at the water's surface where wind effects are dominant. High-frequency radar can be used to measure surface currents, but the range resolution of such radar does not provide details at scales less than a kilometer.

Acoustic waves have been used to detect and map underwater objects such as submarines and ocean floor profiles. It is also known that a sound wave traveling in a fluid contains information about physical properties of the fluid itself. Previous acoustic tomographic techniques have used an inversion method or inverse calculation from the travel time of the acoustic wave to determine properties of the fluid such as temperature, salinity, and density. Other techniques have concentrated on the intensity and amplitude of the acoustic wave as sources of information.

SUMMARY OF THE INVENTION

The invention determines surface or bulk currents using phase information contained in acoustic wave propagated through the fluid. An array of acoustic sources and acoustic sensors is used to obtain a tomographic image of currents in the fluid.

When a sound wave passes between two points through a fluid which has no movement relative to the transmission and receiving points, the sound wave is received at the receiving point with a certain phase for a particular time. However, if there are fluid currents along the acoustic trajectory between the two points, the phase of the acoustic signal can be shifted. Using an eikonal description of acoustic waves propagated through the fluid, relevant information about the current distributions in the fluid may be derived from the phase information of the received acoustic waves.

In a preferred embodiment, an array of coherent underwater acoustic transmitters and receivers are used. The transmitters will typically operate in the 250 to 3000 Hz frequency band, although other frequencies may also be used. Where multiple transmitters will be transmitting simultaneously, the transmitters may each operate at a different frequency. This allows signals from various transmitters to be readily distinguished from one another.

When surface currents are the main object of interest, these transmitter and receiver arrays can be located just beneath the water's surface in an essentially 2-dimensional array. Where bulk currents are of interest, the transmitters and receivers can be located at various depths to form a 3-dimensional array.

The invention can be used in various liquids, but has particular application in bodies of water such as oceans, rivers, lakes and estuaries.

DESCRIPTION OF THE DRAWINGS

FIG. 1b is an elevation view of a simple transmitter and receiver apparatus, similar to that shown in FIG. 1a;

DETAILED DESCRIPTION OF THE INVENTION

Figure 1A:
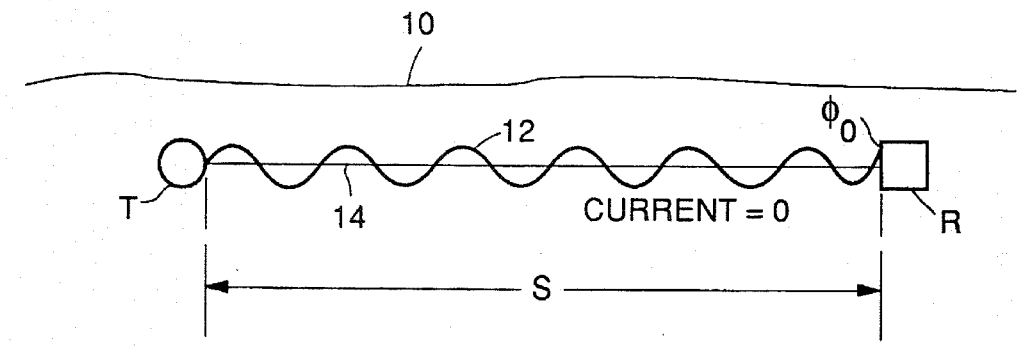
FIG. 1a is an elevation view of a simple transmitter and receiver apparatus useful for explaining the invention's derivation of current information from acoustic phase information.
Figure 1B:
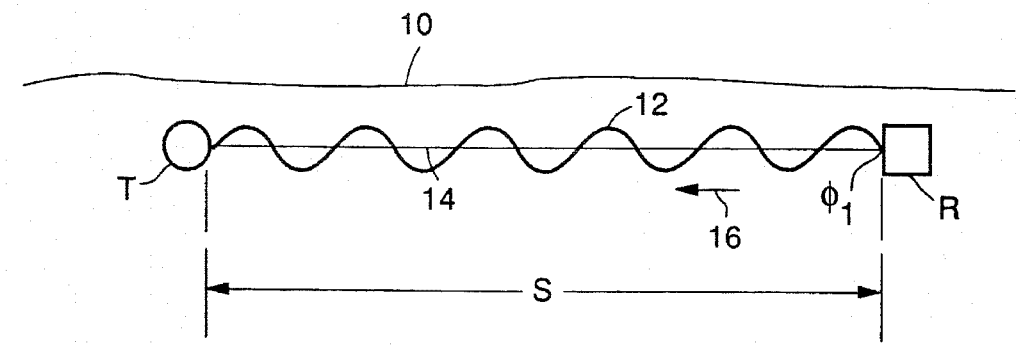

FIGS. 1a and 1b show a transmitter T and a receiver R positioned in a fluid beneath the fluid surface 10. An acoustic signal 12 is propagated through the fluid from the transmitter T to the receiver R. In FIG. 1a there is no fluid current along the unperturbed trajectory 14, so that the acoustic signal 12 is received at an expected phase angle $\phi_0$, which in the example of FIG. 1a is $\pi/2$ or 90° for the time $T_0$. This expected (or zero-current) phase angle $\phi_0$ is a function of the distance s between the transmitter T and receiver R, the phase and frequency of the acoustic signal as transmitted, and the velocity of sound for the fluid.

However, where there is a fluid current along the unperturbed trajectory, the received acoustic signal is received with a phase angle which is shifted from the so-called zero-current phase angle. FIG. 1b shows the transmitter T and receiver R positioned beneath the fluid surface 10, with the fluid having a current 16 along the unperturbed trajectory 14. The passage of the acoustic signal through the areas of current along the unperturbed trajectory is impeded or assisted by the current, depending upon whether the current is in the direction of or against the acoustic signal. In FIG. 1b the current is against the acoustic signal, i.e., the current is in the direction away from the receiver and toward the transmitter. The net velocity of the acoustic signal is thus retarded.

When the acoustic signal 12 is received at the receiver it has a phase angle $\phi_1$, in this case $\pi$ or 180°, which is shifted from the zero-current phase angle $\phi_0$. For the acoustic signal of FIG. 1b, the phase angle is shifted by +90° from the phase angle for the zero-current example of FIG. 1a. Analysis of this phase information gives the average projection of the velocity along the acoustic trajectory.

For a single transmitter and receiver, as shown in FIG. 1a and 1b, it can be difficult to determine the true amount of the phase shift. Because the phase angle can only be measured through one cycle or oscillation, i.e., through 360°, there is the chance that a phase shift may actually be greater than one cycle, or that the phase shift might be negative. For example, a phase shift measured as 90° might actually be a phase shift of 450° or −270°.

To avoid any confusion about the actual versus measured phase shift, the acoustic signal could be a pulsed signal, and any difference in the pulsed signal's travel time (as compared to the zero-current travel time) could be used to determine the actual phase shift. Another alternative is to have the transmitter transmit at several different frequencies and to use the cross-correlated measured phase shifts of all frequencies to determine the actual phase shifts. Another approach makes use of multiple transmitters and receivers with multiple and intersecting acoustic paths; by cross-correlating the information along each acoustic path, the actual phase shifts for each acoustic signal are determined.

Once the actual phase shift is known, the average velocity along the acoustic trajectory between a single transmitter T and single receiver R can be determined. By increasing the number of transmitters and receivers, the current distribution (as opposed to merely the average velocity) along each of several acoustic trajectories can be determined. Through the use of known tomographic techniques, the current distribution within a 2-dimensional or 3-dimensional area can be determined from the phase shifts.

Assuming that the currents change over distances which are large relative to the wavelengths of the acoustic signals that are used to probe them, the effect of the currents on the phases of the acoustic waves can be determined by means of the adiabatic, or eikonal, approximation. In this approximation:

$$\frac{d\vec{r}}{dt} = \nabla_k \omega \tag{1}$$

$$\frac{d\vec{k}}{dt} = -\nabla_r \omega \tag{2}$$

and $$n(\vec{r},t) \sim \frac{1}{\sqrt{k(r)}} \exp[i\vec{k} \cdot d\vec{r}] \tag{3}$$

where ω is the radian frequency of the acoustic wave and is related to k by a known dispersion relation $$\omega = \omega(\vec{k}, \vec{r}) \tag{4}$$

denotes a vector, ∇ is the gradient function, ti is time, i is the complex number symbol, $\vec{k}$ is the wave vector of the acoustic wave, $d\vec{r}/dt$ denotes the group velocity of the acoustic signal, $n(\vec{r},t)$ is the density of the acoustic medium, and $\vec{k}(\vec{r})$ and $k=|\vec{k}(\vec{r})|$ is determined by solving the dispersion relation.

For acoustic waves in a fluid, the dispersion relation is simply $$\omega = kV_s \tag{5}$$

where $V_s$ is the speed of sound. If (a) the fluid is in motion with a position-dependent velocity $\vec{v}(\vec{r},t)$, (b) the distance over which $\vec{v}(\vec{r},t)$ varies is large compared to the acoustic signal length, and (c) the time over which $\vec{v}(\vec{r},t)$ varies is long compared to $\omega^{-1}$, then the dispersion relation of equation 5 can be applied in the frame of reference moving with the fluid as follows:

$$\omega - \vec{k} \cdot \vec{V}(\vec{r},t) = kV_s \tag{6}$$

Then we have $$\nabla \omega = \nabla(\vec{k} \cdot \vec{V}(\vec{r},t)) = (\vec{k} \cdot \nabla)\vec{V}(r,t) + \vec{k} \times (\nabla \times \vec{V}(r,t)) \tag{7}$$

where x is the vector product symbol and ∇x is the curl operation, and $$\frac{d\vec{k}}{dt} = -\nabla \omega = -(\vec{k} \cdot \nabla)\vec{V}(\vec{r},t) - k \times (\nabla \times \vec{V}(\vec{r},t)). \tag{8}$$

To the first order in the velocity field v(r,t), this says that the phase occurring in equation (3), evaluated along an acoustical signal path, is simply $$\int \vec{k} \cdot d\vec{r} \cong k_0 s - \int \frac{ds}{V_s} k_0 V_{k_0}(\vec{r},t) \tag{9}$$

where $k_0 = \omega/V_s$, s is the distance along the unperturbed trajectory, and $V_{k_0}(\vec{r},t)$ is the component of $\vec{v}(\vec{r},t)$ in the direction of the unperturbed trajectory. Accordingly, in the eikonal approximation, the necessary information about the current flow is contained in the phase of the acoustic signal received by the detector when a transmitter transmits an acoustic wave through the region of interest. Using an eikonal approximation for phase information reconstruction, the current flow along the acoustic trajectory can be determined.

With several acoustic sources placed at different locations, the current flow distribution in space can be determined by standard tomographic techniques. Tomographic algorithms permit the extraction of position-dependent quantities from integrals of these quantities along trajectories. Roughly, if there are M sources and N detectors, then M×N position-dependent quantities can be determined in this manner. So for properly placed arrays of acoustic arrays and detectors, the three Cartesian components of the current vector can be determined by (M×N)/3 positions.

Equation (9) shows that the phase change along an acoustical signal path is approximately $$k_0 s - \int \frac{ds}{V_s} k_0 V_{k_0}(\vec{r},t).$$

Thus, if for a 2-dimensional case the region is discretized into an N×M grid, and N×M paths are chosen through the region, there will be N×M values of the phase change along the different paths. The N×M equations giving the phase change in terms of the $V_{k_0}$ at the N×M values of defining the grid coordinates can then be solved for the N×M values of $V_{k_0}$ at the grid coordinates by conventional tomographic techniques, which yield information about the spatial dependence of a quantity in terms of integrals of the quantity. One example of a suitable tomographic algorithm, which employs a matrix inversion for this purpose, is described in Somerstein et al., "Radio frequency geotomography for remotely probing the interiors of operating mini- and commercial-sized oil-shake retorts" *Geophysics*, Vol. 49, No. 8, Aug. 1984, pages 1288–1300.

The use of computer aided tomography (CAT) in medical, geophysical and other applications is well known. One such technique, useful when phase information is of interest, is embodied in this simple equation, which relates the received power at a designated receiver, $P_R$, to the transmitted power$_T$ at a designated transmitter:

$$\frac{P_R}{P_T} = \exp\{-2\int \gamma \cdot dr\} \Gamma^2 K_T^2(\Theta_T) K_R^2(\Theta_R)/r^2 \qquad (10)$$

where $\Gamma^2$=efficiency of the transmitter/receiver pair $\gamma=\alpha+i\beta$= propagation vector $\alpha$= attenuation coefficient $\beta$=phase shift Y=distance between transmitter and receiver $K_T(\Theta_T)$ =(amplitude) gain pattern for transmitter in the direction $\Theta_T$ away from its beam axis.

$K_R(\Theta_R)$=(amplitude) gain pattern for receiver in the direction $\Theta_R$ away from its beam axis.

Equation (10) is equally applicable to the description of acoustic waves as well as electromagnetic waves.

Discretization of equation (10) yields:

$$\sum_{j \cdot R} \alpha_i \Delta r_R = \log_{10}\{P_T \Gamma^2 K_T^2 K_R^2/P_R r_k^2\}/2\log_{10} e. \qquad (11)$$

The index i, enumerates the grid points encountered by the discretized path, and the index k enumerates different paths between the transmitter and receiver. These paths are treated as zero-width beams between the transmitting and receiving devices. Equation (11) is equivalent to a system of linear algebraic equations:

$A x=b$, and the input dataset b is available to measurement. If there were a unique path from transmitter to receiver, the structure matrix A could be obtained and inverted by convergent iterative methods. In the present case, however, this is not true, because hydrophonic devices do not emit narrow beams. The received signal should therefore be regarded as resulting from propagation along several paths between receiver and transmitter.

For clarity, we continue to restrict the description of the process to two spatial coordinates. Then the angular coordinate k is one-dimensional, and the signal detected at the ith receiver from the jth transmitter is obtained as a convolution over the index k.

Equation (11) in this case is of the form:

$$P_{RC}(i,j) = \sum_{K=-\infty}^{+\infty} p(i,j) g(i-K,j) \exp\{-2\Sigma \gamma(ijk) \Delta r(ijk)\} \qquad (13)$$

where $$P_{(i,j)} = P_{Rc} \delta^2 K_{T2}(\Theta_T) K_R^2(\Theta_R) \qquad (14)$$

Here g(n) is a window function introduced to minimize spurious effects due to discretization. One example of such a window function is the Hamming window defined by:

$$g(m)=0.54-0.46 \cos\{2\pi n/(k-1)\} \text{ for } m=0,1 \ldots k-1 \qquad (15)$$

The limits of summation in equation (14) are extended to plus or minus infinity, because the window function vanishes outside the beam width.

$$P_{RC}(i,j) = \sum_{k=-\infty}^{\infty} \bar{p}(i,j,k) g(i-k,j) \qquad (16)$$

where $\bar{P}(i,j,k)=p(i,j)\exp\{-\xi\partial(i,j,(e)(17)\alpha(i,j)\}$

Because equation (13) is of convolution type, the solution can be effected very efficiently by the Discrete Fourier Transform method. The result is:

$$\bar{P}(z)=P_{RC}(Z)/G(Z) \qquad (18)$$

$$z = \exp\left(\frac{i2\pi k}{N}\right)$$

where and N is the dataset size $\bar{P}(Z)$, $P_{RC}(Z)$ and G (Z) are FFT's of, $\bar{P}$(on index k), $P_{RC}(i,j)$ and g(k) respectively.

By reversing the Fourier Transform we can now obtain a space sequence:

$$\bar{P}(i,j,k)=P(i,j)\exp\{-\Sigma Y(ijk)\alpha Y(i,j)\} \qquad (19)$$

which gives the signal through a single path. Index i labels the receiver j labels the transmitter, and k labels the path.

To complete the solution, replace P with $\bar{p}$ in equation (11), which then describes a zero width path. In this case the "algebraic iterative reconstructive technique" such as described by the following articles; R. Gordon., 1974, entitled "A tutorial on ART (algebraic reconstruction techniques): Trans. Inst. of Elect. & Electron. Engineers, Nucl., Sci., NS-21, 78–93, G. T. Herman, A. Lent and S. W. Rowland, 1973 entitled, ART: Mathematics and Applications (A report on the mathematical foundations and of the applicability to real data of the algebraic reconstruction techniques), Journal of Theoretical Biology, Vol. 42, pages 1 –32, and the article to D. L. Lager and R. J. Lytle, entitled "Determining a subsurface electromagnetic profile from high frequency measurements by applying reconstruction technique algorithms: Radio Science, Vol. 12, pages 249–260, is directly applicable and produces best-fit estimates of the propagation vector Y as a function of spatial coordinates, along that particular path. Since there are multiple receivers and multiple transmitters, the M×N paths can be chosen in such a way as to span the whole region with any reasonable resolution cell.

The foregoing discussion of the proposed method is applicable to any kind of wave propagation in an inhomogeneous medium. To relate the result to propagation of acoustic waves, simply refer back to equation (9) where it is clear that the total phase shift:

$$i_{R_O S^{-i}} \int \frac{ds \cdot R_o}{V_S} V_{R_1}(r,t) \qquad (20)$$

is to be identified with the imaginary part of $\gamma dr$ in equation (10). Attenuation of acoustic waves (i.e., the real part of $\gamma$) can also be obtained as a by-product.

In applications where the sources operate simultaneously, each source may be operated at a different frequency from the other sources. In this way, signals from different sources may be distinguished from each other, so that there is no ambiguity about the origin of a signal received at a detector. Preferred frequencies are in the band extending from about 250 to 3000 Hz. However, other frequencies may also be used, depending upon the particular application.

A precise knowledge of the distance s between the transmitters T and receivers R is important. As one option, all transmitters and receivers can be firmly anchored in position, as where the transmitters and receivers are secured to fixed platforms such as dock pilings or rigidlysecured buoys. Another option is to employ a system to precisely track the positions of all transmitters and receivers, and adjust the values of s to compensate for any changes in position.

Figure 2:
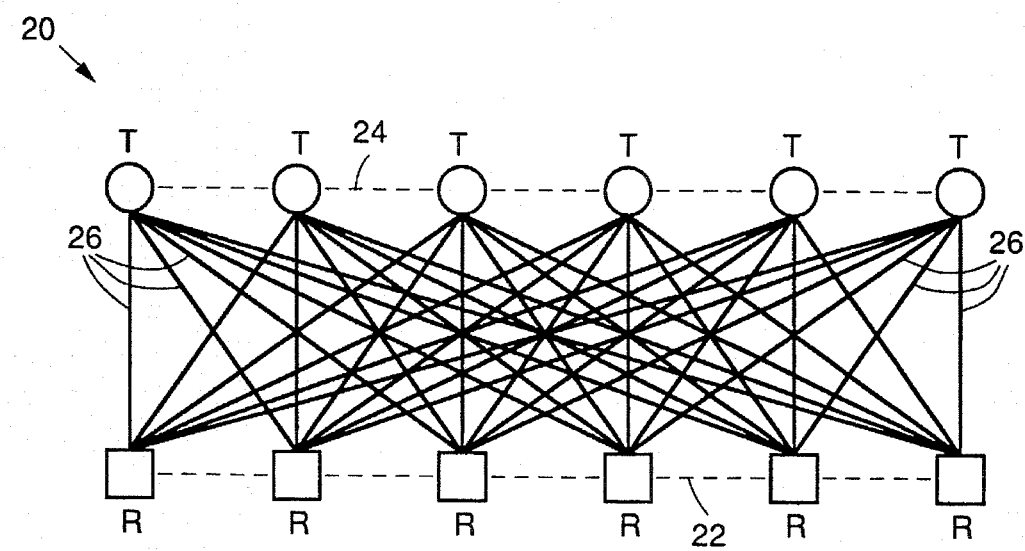
FIG. 2 is a top plan view of one embodiment of the invention comprising a 2-dimensional array of transmitters and receivers.

FIG. 2 shows one embodiment of the invention. The apparatus 20 shown comprises a 2-dimensional array of receivers R and transmitters T. The array includes a line 22 of receivers R and a line 24 of transmitters T. The acoustic paths 26 run from each transmitter to each receiver. Thus, the apparatus 20 covers an area loosely defined at its opposite edges by the transmitters T and receivers R. The outer regions of the area near the transmitters and receivers have a lower density of acoustic paths 26 than the central region. To ensure that sufficient information is gathered, the array preferably extends beyond the boundaries of the region of significant interest.

A 2-dimensional array such as that shown in FIG. 2 will determine velocity distributions only in the plane of the array. That is, velocity distributions will be determined in only two dimensions. Given M sources and N detectors, M×N position-dependent quantities can be determined. For 2-dimensional arrays, the two planar components of the current vector can be determined at (M×N)/2 positions. Thus, for the 6×6 array shown in FIG. 2, the two planar components of the current vector can be determined at 18 positions.

Figure 3:
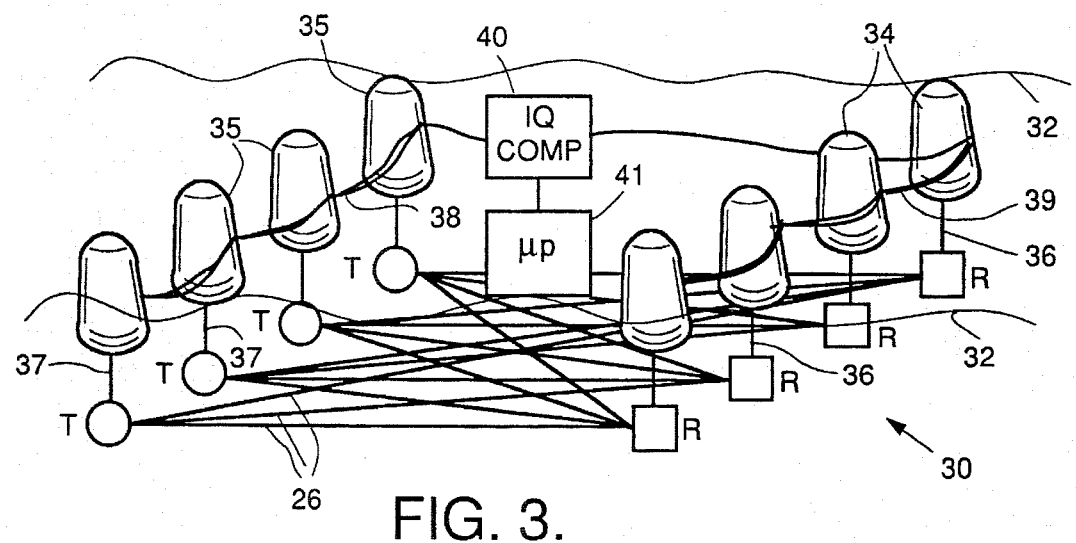
FIG. 3 is a perspective view of another embodiment of the invention comprising a 2-dimensional array of transmitters and receivers positioned beneath the surface of a body of water.

FIG. 3 shows another embodiment, similar to that shown in FIG. 2, in which the system 30 comprises an essentially 2-dimensional array of transmitters T and receivers R located just below the water's surface 32. Such an array is useful for determining surface currents. The receivers R and transmitters T are shown suspended underneath respective buoys 34 and 35 by respective lines 36 and 37. The receivers R may be of a variety of types, so long as they can operate in an underwater environment. Hydrophones are effective receivers for the underwater applications of this invention.

The determination of the phase differentials between the transmitted and received signals can be performed at any convenient location, such as on one of the transmitter or receiver buoys, on a separate buoy or floating platform, or on land if close enough. There is a similar latitude in locating a site for calculating the fluid currents once the phase differentials are known, although typically both functions will be performed at the same location. A conventional IQ comparator can be used to determine the phase differentials, and a standard computer for the current calculation. In FIG. 3, signals corresponding to the transmitted signals are delivered from the transmitters T to their respective buoys 35, such as by a fiber optic linkage, while the received signals are delivered from the receivers R to their buoys 34. The optical fibers from the transmitted T and receivers R are bundled in respective fiber optic cables 38 and 39, which deliver the signals to an IQ comparator 40 or other mechanism for determining the phase differentials. The phase differential output from IQ comparator 40 is delivered to a computer microprocessor 41 that is programmed to perform the tomographic algorithm that calculates the fluid currents. This information can then be transmitted by another fiber optic cable (not shown) to a desired pickup location. Communications channels other than fiber optics, such as RF broadcasts from the transmitter and receiver buoys to a computation station and from the computation station to a separate monitoring location, could also be employed.

The array as shown includes four receivers R and four transmitters T. However, this is merely one example of a potential array; the specific numbers and positions of the transmitters and receivers is dependent upon the particular application.

Figure 4:
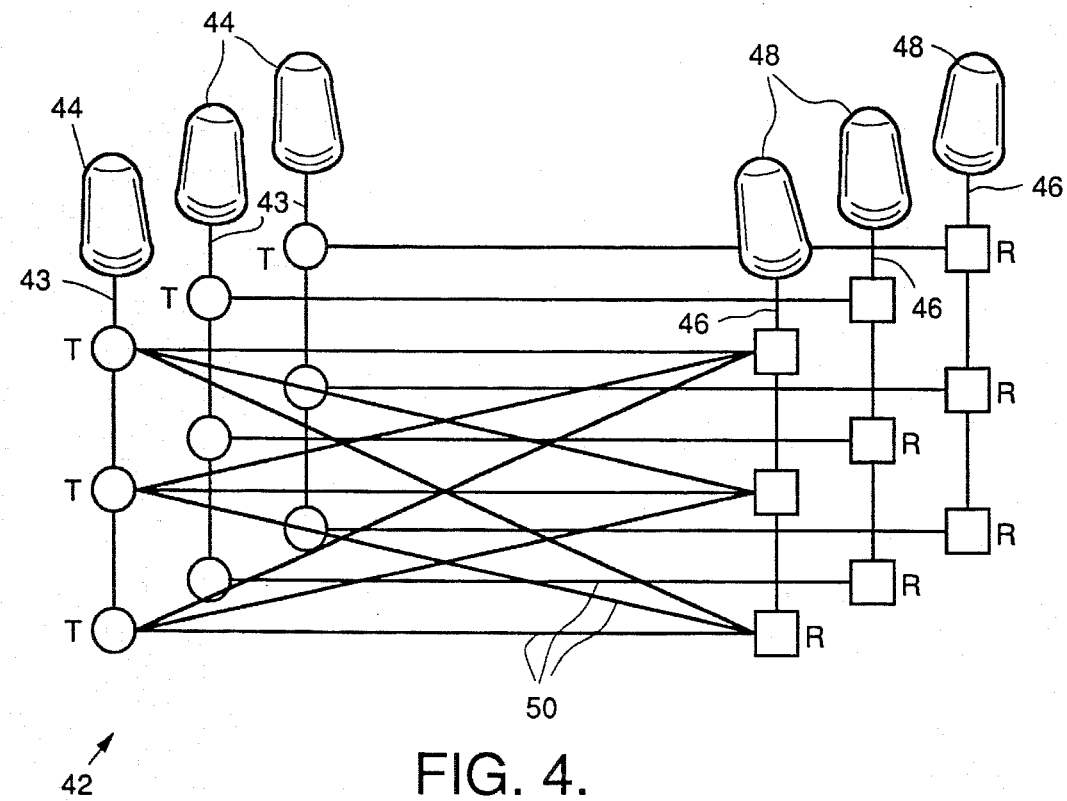
FIG. 4 is a perspective view of a further embodiment of the invention which includes a 3-dimensional array of transmitters and receivers for determining bulk currents.

FIG. 4 shows a system 42 which comprises a 3-dimensional array such as may be used in determining bulk currents. In the embodiment shown, a series of transmitters T are suspended on a line 43 at varying depths beneath each floating transmission buoy 44. Similarly, a series of receivers R are suspended on a line 46 beneath each floating receiver buoy 48. A communications link between both the transmitters and the receivers and a computation station, such as a fiber optic network similar to that illustrated in FIG. 3, would also be included.

The acoustic tranjectories 50 between transmitters and receivers cover a 3-dimensional region that is roughly enclosed at the water's surface 32 by the buoys 44, 48. In the illustration of FIG. 4, in which nine total transmitters and nine total receivers are used, the three Cartesian components of the current vector can be determined at (9×9)/3, or 27, positions.

It should be noted that essentially any number and combination of transmitters and receivers may be used. The choice of numbers and positions for the transmitters and receivers depends upon the specific application. For example an array used for monitoring currents in an estuary will normally have a different physical layout than an array used for monitoring near-shore ocean currents. In general, with increased numbers of transmitters and receivers, more precise current distribution information may be obtained.

The above described embodiments are intended to illustrate the principles of the invention, but not to limit its scope. Other embodiments and variations will be apparent to those skilled in the art, and may be made without departing from the spirit and scope of the invention as defined in the following claims.

We claim:

1. A system for determining fluid currents, comprising:
   at least one transmitter for transmitting acoustic signals through a fluid, said fluid having a surface;
   at least one acoustic receiver for receiving said transmitted acoustic signals;
   means for determining the phases of said transmitted acoustic signals as received by said receiver relative to said transmitted acoustic signals phases wherein said means for determining said phases of said transmitted acoustic signals employs an eikonal approximation; and
   means for calculating a current flow distribution within said fluid between said transmitter and receiver based upon said acoustic signal phases, wherein said calculating means calculates said current flow distribution from said acoustic signal phases by a tomographic calculation.

2. The system of claim 1, wherein said transmitter transmits acoustic signals at different frequencies.

3. The system of claim 2, wherein said transmit acoustic signals at frequencies within the approximate range of 250 to 3000 Hz.

4. The system of claim 1, wherein said acoustic receiver comprises a fiber optic hydrophone.

5. The system of claim 1, wherein said transmitters and receivers are positioned in an approximately planar configuration, thereby forming an approximately 2-dimensional array.

6. The system of claim 5, wherein said transmitter and receiver are each located beneath said fluid surface, whereby the system determines fluid currents beneath said fluid surface.

7. The system of claim 1, wherein said transmitter and said receiver are positioned at different depths beneath said fluid surface, thereby forming a 3-dimensional array.

8. The system of claim 7, wherein said transmitter and said receiver are suspended beneath said fluid surface attached to floating buoys.

9. A method of determining fluid currents within a fluid, said fluid having a surface, comprising the steps of:
   transmitting at least one acoustic signal through said fluid from a transmission location within said fluid;

receiving the transmitted acoustic signal at at least one receiving location within said fluid;

determining the phase of said transmitted acoustic signal as received at said receiving location relative to said transmitted acoustic signal phases at said transmission location, wherein said phase determination employs an eikonal approximation; and calculating a current flow distribution within said fluid between said transmission and receiving locations based upon said acoustic signal phases, wherein said current flow distribution calculation applies phase determination in conjunction with a tomographic calculation.

10. The method of claim 9, wherein said transmitted acoustic signal is transmitted from a different transmission location at different frequencies.

11. The method of claim 10, wherein said transmitted acoustic signals are transmitted at a frequency within the approximate range of 250 to 3000 Hz.

12. The method of claim 10, wherein said transmitted acoustic signal is received at multiple receiving locations.

13. The method of claim 12, wherein said receiving and transmitting locations are positioned beneath said fluid surface, thereby forming an approximately 2-dimensional array beneath said fluid surface to determine fluid currents beneath said fluid surface.

14. The method of claim 12, wherein said receiving and transmitting locations are positioned at various depths beneath said fluid surface, thereby forming a 3-dimensional array.

* * * * *